United States Patent [19]

Ladell

[11] 4,199,678

[45] Apr. 22, 1980

[54] ASYMMETRIC TEXTURE SENSITIVE X-RAY POWDER DIFFRACTOMETER

[75] Inventor: Joshua Ladell, Monsey, N.Y.

[73] Assignee: U.S. Philips Corporation, New York, N.Y.

[21] Appl. No.: 7,880

[22] Filed: Jan. 31, 1979

[51] Int. Cl.² ............................................. G01N 23/20
[52] U.S. Cl. ............................ 250/272; 250/277 CH
[58] Field of Search ........ 250/272, 273, 274, 277 CH, 250/275

[56] References Cited

U.S. PATENT DOCUMENTS 3,509,336  4/1970  Wilchinsky et al. ......... 250/277 CH

Primary Examiner—Craig E. Church
Assistant Examiner—Thomas P. O'Hare
Attorney, Agent, or Firm—Thomas A. Briody; Jack Oisher; Paul R. Miller

[57] ABSTRACT

An interactive computer controlled asymmetric texture-sensitive parafocussing X-ray powder diffractometer employs an incremental rotating specimen device which permits azimuthal rotation (through the angle $\phi$ of the disc-shaped specimen about its surface normal. The rotating specimen device, rotatable about the principal diffractometer axis, can be offset an angle $\alpha$ from the symmetric position in which the specimen surface normal makes the angle $(90-\theta)°$ with both the source-to-specimen and detector-to-specimen directions. In order to maintain the Brentano focussing condition, the photon-counting detector is supported on a slide which is translated towards or away from the specimen by a stepper-motor drive lead screw. K, the ratio of the detector-to-specimen and x-ray source-to-specimen distances is constrained to the specified range $c<K<f$, where c is the smallest and f the largest ratio achieved. The focussing condition is realized by computer control which maintains $K=\sin(\theta+\alpha)/\sin(\theta-\alpha)$ and modifies the measured intensity by multiplying its value by $0.5(K+1)K^{0.75}\exp[\mu R(K-1)]$ where R is the source-to-specimen distance, and $\mu$, the linear absorption coefficient for air.

6 Claims, 7 Drawing Figures

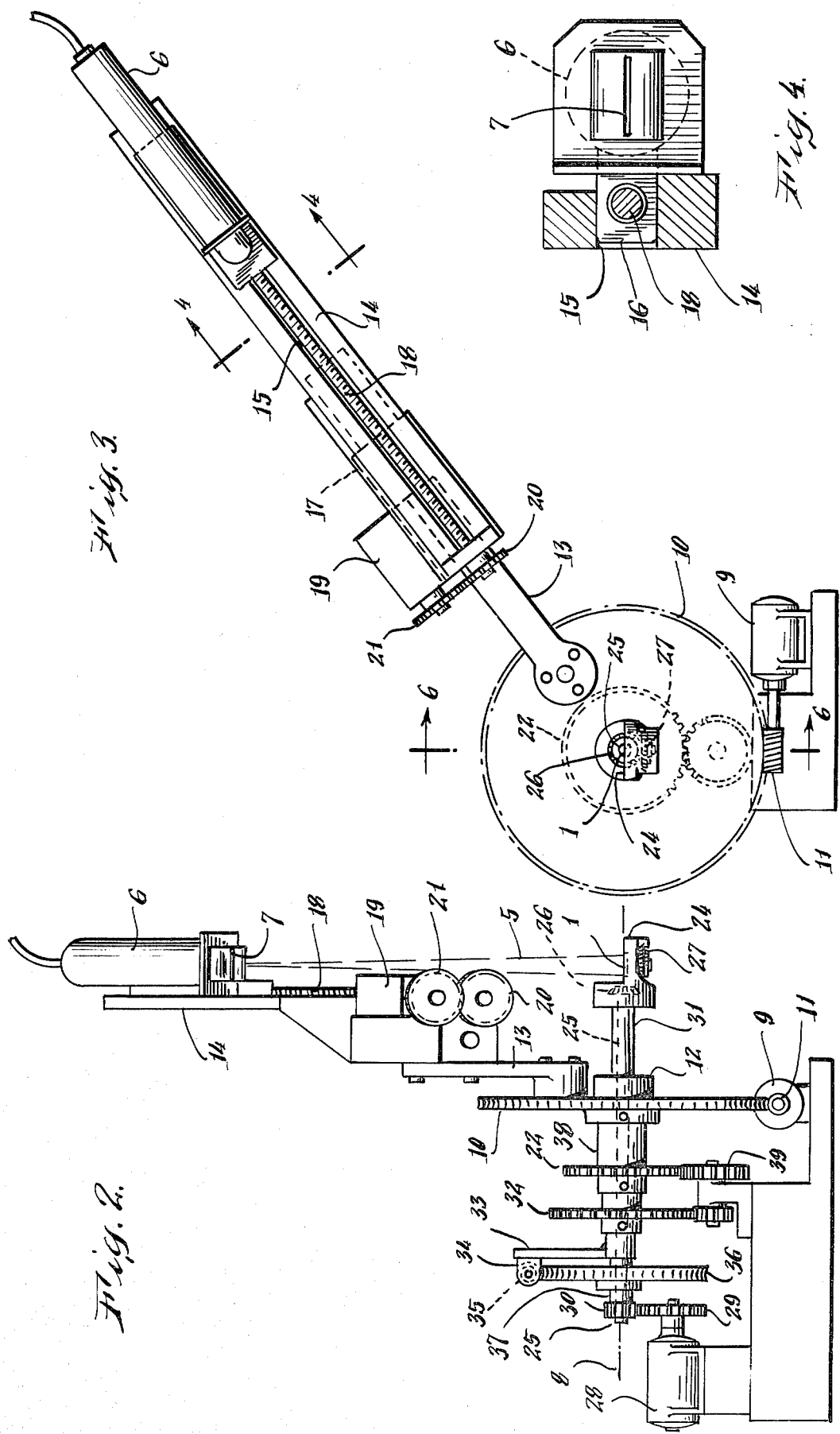

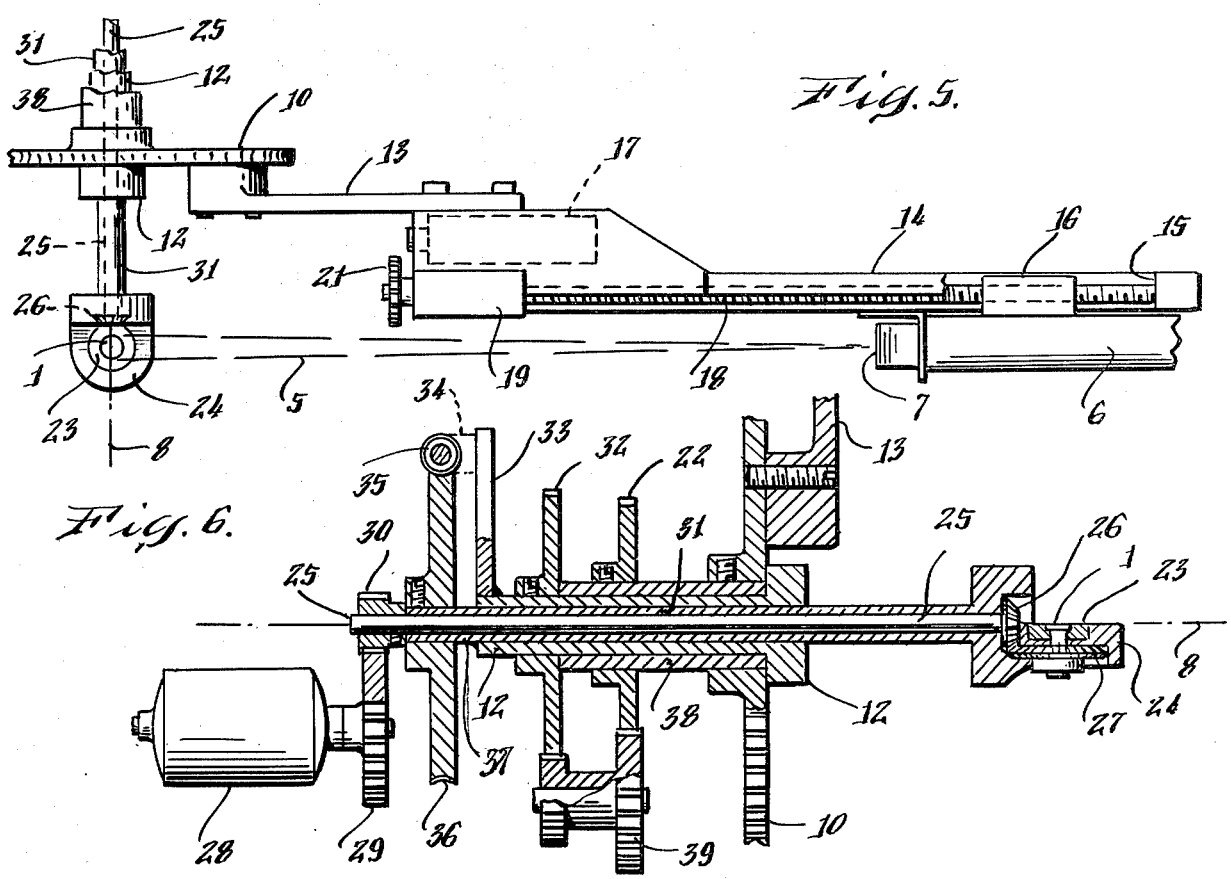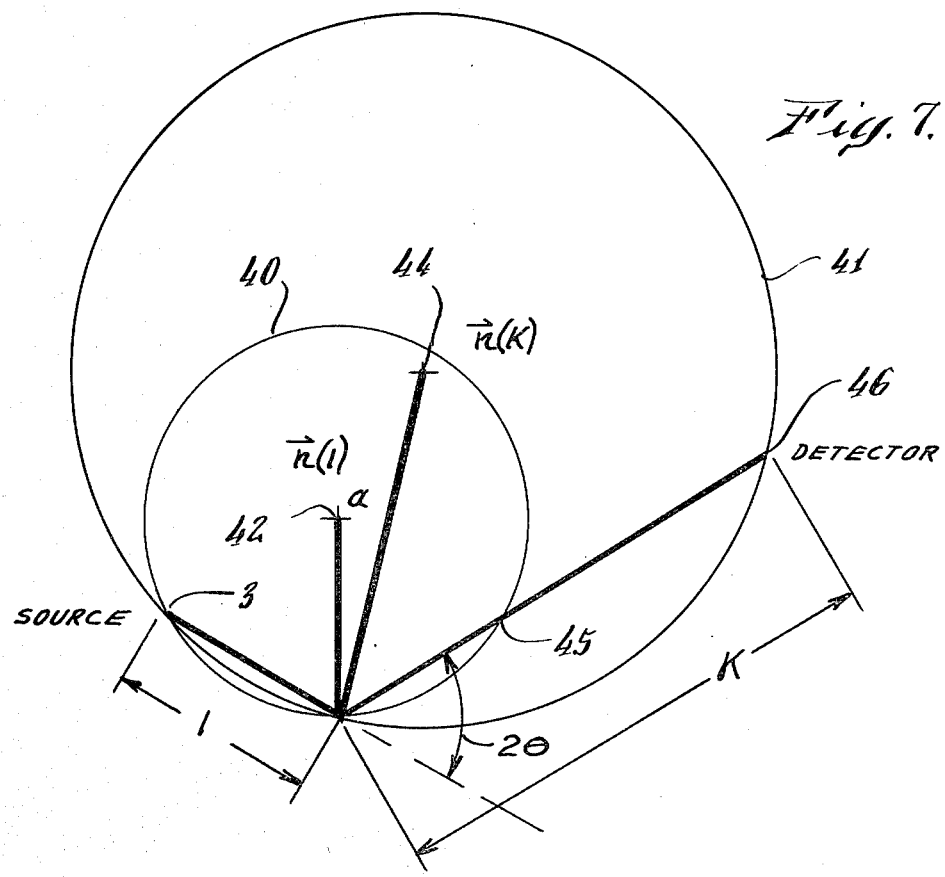

ASYMMETRIC TEXTURE SENSITIVE X-RAY POWDER DIFFRACTOMETER

BACKGROUND OF THE INVENTION

My invention relates to an x-ray powder diffractometer and in particular to a diffractometer for determining the structure and texture of a powder sample mounted for rotation in the path of a beam of monochromatic X-rays and a photon detector.

The standard powder X-ray diffractomer, described by W. Parrish, E. W. Hamacher and K. Lowitzsch, Philips Technical Review, 16, pp 123-133 (Oct. 1954) employs the Bragg-Brentano symmetric parafocussing geometry, maintains a flat specimen equi-distant from the X-ray focal source and the photon-counting detector. Diffraction spectra are measured with the diffraction vector virtually collinear with the surface normal. High quality intensity data are measureable in this arrangement only if the sample comprises a large number of randomly oriented small crystalline particles.

Two specimen related effects contribute to the degradation of the accuracy of the measured intensity as characteristic of the diffracting material. The first, or "particle statistics" (number of particles in the diffracting position) effect is manifest when the size distribution of the crystallites is such that the diffracting volume varies intractably with $2\theta$. The second effect is manifest when the crystallites are not randomly oriented, but are instead distributed in some "preferred orientation". Both effects can be avoided in such cases where some control can be exercised over the sample preparation.

A symmetrical focussing reflection method described by L. G. Schulze in Journal of Applied Physics, 20, p. 1030-1033, (November 1949) involves a departure from the foregoing method involving employing narrow horizontal slits to collimate the incident beam into a flat wedge, i.e. to collimate the incident beam into parallelism in the vertical direction but still diverging in the horizontal plane. The sample was also mounted for rotation about an axis normal to its surface and rotation of the sample holder about an axis collinear with the X-ray focal source to detector displacement. This method permitted determining pole figures of flat samples with a Geiger or scintillation counter spectrometer.

SUMMARY OF THE INVENTION

It is an object of this invention to provide a new X-ray diffractometer for making structure determinations of powder samples yielding more information than heretofore thought possible.

Since the acquisition of accurate intensities is indispensable to effective analytic procedures in modern powder diffractometry, the invention employs a computer to control an asymmetric powder diffractometer so as to reveal the extent of the aforesaid effects and to provide a means for their correction. By utilizing the principal of asymmetric focussing, in which the specimen is independently rotatable about the principal diffractometer axis, coupled with means for rotating the specimen about the specimen surface normal, the constraint of having the diffraction vector collinear with the specimen surface normal is removed, permitting the generation of diffractograms with diverse orientations of the specimen with respect to the diffraction vector.

The asymmetric capability is achieved by modifying the standard diffractometer (ibid) to effect the following changes:

1. A stepper motor is employed to drive the rotating specimen about its surface normal effecting changes of the azimuthal orientation (measured by $\phi$) in 4 degree steps.

2. A stepper motor (or protractor device for manual operation) permits independent angular displacement (measured by the angle $\alpha$) of the specimen post about the principal diffractometer axis. This permits the specimen surface normal to be offset $\alpha$ from the symmetric position (where the surface normal is at $(90-\theta)°$ from both the incident and diffracted beam directions).

3. The photon-counting detector is mounted on a slide which is translateable towards or away from the specimen by a stepper-motor driven lead screen). K, the ratio of the detector-to-specimen and X-ray source-to-specimen distance is constrained to the range $c<K<f$ where c is the smallest and f the largest ratio achieveable. The smallest ratio must be at least 1. (Note, if K equals 1, the instrument becomes a symmetric diffractometer as described by Parrish, et al). This condition in which the asymmetric diffractometer collapses into a conventional symmetric diffraction cannot be met by Schulze.

4. A computer controls each of the stepper motor drives, including one which can rotate the detector about the principal instrument axis at twice the speed of the specimen while maintaining $K = \sin(\theta+\alpha)/\sin(\theta-\alpha)$ and modifies the measured photon intensity by multiplying its value by $0.5 (K+1) K^{0.75} \exp[\mu R (K-1)]$, where R is the source-to-specimen distance, and $\mu$ the linear absorption coefficient for air. This satisfies the focussing condition for diffraction occurring at the scattering angle $2\theta$ when the specimen surface normal is displaced $\alpha$ from the diffraction vector. For the permitted range $(c<K<f)$, the measurable Bragg diffraction angles are determined by $$\theta > \tan^{-1}\left\{ \frac{(f+1)}{(f-1)} \tan \alpha \right\} \text{ or }$$

$$\theta > -\tan^{-1}\left\{ \frac{(c+1)}{(c-1)} \tan \alpha^- \right\}$$

The intensity correction formula given above assumes the use of a theta compensating slit which constrains the source slit width to irradiate a constant area on the specimen at all $2\theta$ angles.

DESCRIPTION OF THE DRAWING

The invention will be described further with reference to the accompanying drawing in which:

FIG. 2 is a side view in elevation showing the specimen drive mechanism and detector drive mechanism.

FIG. 3 is an end-view in elevation showing the specimen and detector drive mechanism.

FIG. 4 is a detail view of the detector drive mechanism.

FIG. 5 is a plan view of the detector drive mechanism.

FIG. 6 is an elevational view partly in section of the sample drive mechanism.

FIG. 7 is a diagram illustrating the geometry of the parafocussing system.

DETAILED DESCRIPTION OF THE INVENTION

Figure 1:
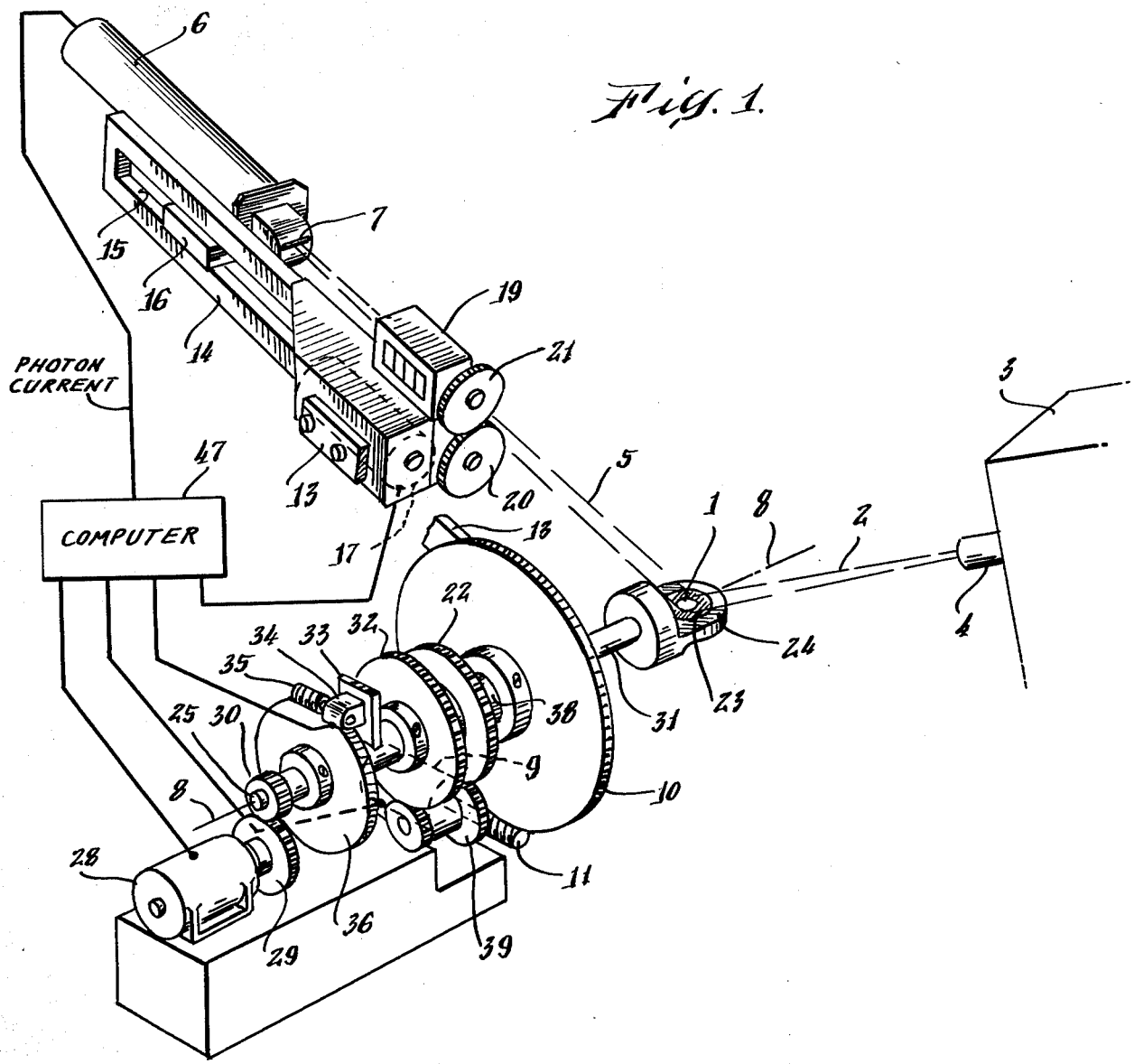
FIG. 1 shows in perspective the diffractometer with the specimen mounted for rotation about an axis in the plane of the specimen and an axis normal to the plane of the specimen.

The diffractometer according to the invention is that described in U.S. Pat. No. 2,549,987, generally known as a Norelco High Angle Goniometer, modified to permit azimuthal rotation (through the angle $\theta$) about its surface normal. As shown in FIG. 1, a powder specimen 1 receives incident X-rays 2 from a source 3 of monochromatic X-radiation. In view of the geometry of this device, a line source of radiation may be used, rather than a point source as required in the device described by L. G. Schulze in the Journal of Applied Physics, referred to above. This line source is viewed, from the specimen, through a parallel slit collimator 4, known as Soller slits, which effectively breaks up the line source into a plurality of point sources of limited vertical divergence.

X-rays 5 diffracted, or reflected by the specimen, are received by a photon counting detector 6 after passing through receiving slit 7 for limiting the divergence of the diffracted beam. The detector 6 and specimen 1 are mounted for rotation about a common axis 8, the detector rotating at twice the speed of the specimen so that as the specimen rotates through an angle $\theta$, the detector rotates through an angle $2\theta$. This rotation is produced by a stepping motor 9 coupled to a worm wheel 10 by a worm 11 mounted on its shaft. Gear wheel 10 and spur gear 22 are both rigidly fastened to hollow shaft 38. Worm wheel 10 is coupled to an arm 13 carrying a bracket 14 having a guide 15 in which a flange 16 for supporting detector 6 is slideable.

Detector 6 driven by a stepper motor 17 and a lead screw 18 moves away from and/or toward the specimen along bracket 14. A mechanical counter 19 driven by a gear 20 coupled to a gear 21 which is coupled to the lead-screw 18 records the distance travelled by the detector.

Specimen 1 is rotated about axis 8 by hollow shaft 12 driven by motor 9 at half the speed ($\theta$) of rotation of the detector 6 by gear wheel 22. The rotation of 22 is halved by its linkage to the two gear subassembly 39.

The device thus far described is a standard X-ray diffractometer except that the detector is slideable on an arm away from and toward the specimen and the specimen is always symmetrically disposed in relation to the detector and X-ray source. In this arrangement, the specimen rotates at half the speed of rotation of the detector and reflects incident X-rays at various angles to the detector. The only constraint in this system is the requirement that the detector rotate at twice the speed of rotation of the specimen.

In order to understand the invention better, reference is made to FIG. 7 where the source 3 and the center of specimen 1, are on the intersection of two focussing circles 40 and 41, the centers of which are at 42 and 44, respectively. Circle 40 is schematic for the standard symmetric diffractometer. To achieve focussing for the symmetric case, the detector is placed at position 45 and the flat specimen oriented so that its surface normal is collinear with n(1). Focussing is also achievable (the asymmetric case) by moving the detector to position 46 on circle 41, and orienting the specimen surface normal to point along n(K) to center 44. For both cases, the diffraction vector is collinear with n(1). Thus, for the symmetric case the diffraction vector is collinear with the specimen surface normal, whereas in the asymmetric case, the diffraction vector is angularly displaced from the surface normal for the angle $\alpha$. Suppose that the sample exhibits preferred orientation with crystallites tending to be oriented such that a reflecting set of planes is normal to the specimen surface, then for the symmetric case described above the intensity will be very much enhanced since for this case the diffraction vector and the direction of preferred orientation are collinear. For the asymmetric setting, however, the diffraction vector collinear with n(1), is offset $\alpha$ degrees from the surface normal n(K). Accordingly, if the diffraction effects were measured in both the symmetric and asymmetric modes it would be apparent that there was preferred orientation. On the other hand, if the specimen did not exhibit preferred orientation, then the diffraction measured in both the asymmetric and symmetric modes would be the same apart from a known intensity attenuation in the asymmetric case.

In order to properly scan the sample, the detector must be displaced so that $$K = \sin(\theta + \alpha) / \sin(\theta - \alpha)$$

Since the detector is constrained to move towards or away from the specimen within the range e.g.

$$1 \leq K \leq 3$$

where K is the ratio of the detector-to-specimen and X-ray source-to-specimen distances, the measurable Bragg diffraction angles are restricted such that $$\theta > \tan^{-1}(2 \tan \alpha)$$

For a specimen having uniform "particle statistics" as well as randomly oriented particles, it can be shown that the intensity I (k) is:

$$I(k) = \frac{2I(1)\exp(\mu R(1-K))}{(K+1) K^{0.75}}$$

where I (1) is the intensity for the symmetric case (K=1), R is the X-ray source-to-specimen distance and $\mu$ the linear absorption coefficient for air.

In order to rotate the specimen 1 about its surface normal, the specimen is placed on a turntable 23 in a cup-shaped holder 24 and rotated by a shaft 25 carrying a set of bevel gears 26 and 27 driven by a motor 28 which drives shaft 25 through gears 29 and 30.

Shaft 25 rotates within a hollow sleeve 31, which in turn rotates within hollow sleeve 12. Sleeve 12 supports a bracket 33 which supports a stepper motor 34 which drives a worm 35 coupled to worm wheel 36 which rotates shaft 31 moving the specimen through the angle $\alpha$, which is the angular displacement between the orientation of hollow shaft 12 relative to the orientation of hollow shaft 31. Hollow shaft 12 is linked via gear subassembly 39 and gear 22 to hollow shaft 38 which in turn is rigidly fastened to worm wheel 10. When $\alpha = 0$, the orientation of specimen cup 24 is in the same position as would be manifest in a standard diffractometer.

Motors 9, 17, 28 and 34 must be controlled such that for a fixed angular displacement $\theta$, and scattering angle $2\theta$, K is automatically set to $\sin(\theta + \alpha)/\sin(\theta - \alpha)$ to create or maintain the Bragg-Brentano asymmetric parafocussing condition. Also the value of the measured intensity of diffraction must be modified by the factor $0.5\ (K+1)K^{0.75}e^{\mu R(K-1)}$ to account for the geometric attentuation. This is accomplished by a computer 47 which also scales detected X-ray photons. Under computer control, for a fixed angular displacement $\alpha$, K is automatically set and the detector moved along the bracket 14 while the specimen 1, and detector 6 are rotated. Let I $(\alpha, \phi, \theta)$ represent the intensity measured at a scattering angle $2\theta$, with the diffraction vector displaced an angle $\alpha$ from the surface normal and the projection of the diffraction vector in the specimen surface plan azimuthal displaced an angle $\phi$. If the sample is free of "particle statistics" of preferred orientation, the condition to be met is that I $(\alpha, \phi, \theta)$ is virtually constant with $\phi$ and $\alpha$. If I $(\alpha, \phi, \theta)$ oscillates with $\alpha$ and/or $\phi$, this indicates a "particle statistic" effect. In this case the characteristic intensity is obtained from average values measured for different values of $\alpha$ and $\phi$. If $(\alpha, \phi$ and $\theta)$ increase or decrease monotonically with $\alpha$ this is evidence of a preferred orientation in the sample.

In this manner not only can the texture of the sample be determined as well as the structure, but phase separation and indexing by identifying lines of common $\alpha$ or $\phi$ dependence.

Unlike the standard rotating specimen device in which the azimuthal angle $\phi$ is altered by means of a continuously rotating synchronous motor, in accordance with this invention a stepper motor (28) is used to change the azimuthal angle. By causing the stepper motor under computer control to rotate the specimen an integral number of revolutions during each increment of $2\theta$ advancement, statistical averaging of the azimuthal distributions can be accomplished which is consistent at all $2\theta$ angles. Thus, the advantages of averaging out particles statistics are realizable without modifying irrationally the relative intensities measurable at different $2\theta$ angles.

What is claimed is:

1. A diffractometer comprising a source of X-radiation, a support for positioning a disc-shaped specimen in the path of X-radiation from said source and rotatable about a given axis normal to the surface of the specimen, a detector positioned to receive X-rays diffracted by said specimen, means to rotate the specimen an angle $\alpha$ from the symmetric position in which the specimen surface normal makes the angle $(90-\theta)°$ with both the source-to-specimen and detector-to specimen directions in the plane formed by the incident and diffracted beams such that the specimen normal remains in the plane, slide means for supporting the detector for rectilinear movement towards or away from the specimen, means to move the detector step-wise towards or away from the specimen while constraining the ratio K of the detector-to-specimen and X-ray source-to-specimen distance, means to rotate the slide about the specimen, and means for maintaining $K=\sin(\theta+\alpha)/\sin(\theta-\alpha)$ where $\theta$ is the Bragg diffraction angle, while modifying the measured intensity by multiplying its value by $0.5\ (K+1)\ K^{0.75}\exp[\mu R\ (K-1)]$, where R is the source-to-specimen distance and $\mu$, the linear absorption coefficient for air.

2. A device as claimed in claim 1 in which the means for maintaining $K=\sin(\theta+\alpha)/\sin(\theta-\alpha)$ while modifying the measured intensity by multiplying its value by $0.5\ (K+1)\ K^{0.75}\exp[\mu R\ (K-1)]$ is a computer responsive to photon current from the detector and coupled to each of the means for moving the specimen and the detector and responsive to said means for modifying the measured intensity of reflection from the specimen as determined by the photon current generated by the detector.

3. A device as claimed in claim 2 which the detector moving means is a stepper-motor drive and lead screw.

4. A device as claimed in claim 2 in which the means for rotating the specimen from the symmetric position is a stepper motor coupled to a holder for the specimen by driving means.

5. A device as claimed in claim 4 in which the driving means include a shaft within a hollow sleeve coupled to the specimen holder by spur gears.

6. A device as claimed in claim 2 in which the specimen is rotated about an axis normal to the surface of the specimen by a stepper motor which is coupled to and controlled by the computer.

* * * * *